United States Patent [19]

Bell

[11] 4,161,516

[45] Jul. 17, 1979

[54] COMPOSITION FOR TREATING AIRWAY DISEASE

[75] Inventor: John H. Bell, Loughborough, England

[73] Assignee: Fisons Limited, London, England

[21] Appl. No.: 759,469

[22] Filed: Jan. 14, 1977

Related U.S. Application Data

[63] Continuation-in-part of Ser. No. 599,071, Jul. 25, 1975, abandoned.

[30] Foreign Application Priority Data

Jan. 23, 1976 [GB] United Kingdom ................. 2606/76
Jan. 23, 1976 [GB] United Kingdom ................. 2608/76

[51] Int. Cl.[2] ......................... A61J 3/00; A61K 31/35

[52] U.S. Cl. ....................................... 424/14; 424/283

[58] Field of Search ..................... 260/345.2; 424/283, 424/14

[56] References Cited

U.S. PATENT DOCUMENTS

| | | | |
|---|---|---|---|
| 3,419,578 | 12/1968 | Fitzmaurice et al. | 260/345.2 |
| 3,634,582 | 1/1972 | Hartley et al. | 424/14 |
| 3,957,965 | 5/1976 | Hartley et al. | 424/14 |

*Primary Examiner*—V. D. Turner
*Attorney, Agent, or Firm*—Merriam, Marhsall & Bicknell

[57] ABSTRACT

There is described a medicament in pellet form characterized in that the pellet is soft, is from 10 to 1,000, preferably 30 to 500 microns, in diameter and comprises an agglomeration of individual medicament particles at least 90%, and preferably at least 95%, by weight of which have a diameter of less than 10 microns. Processes for making the soft pellets are also described.

16 Claims, 8 Drawing Figures

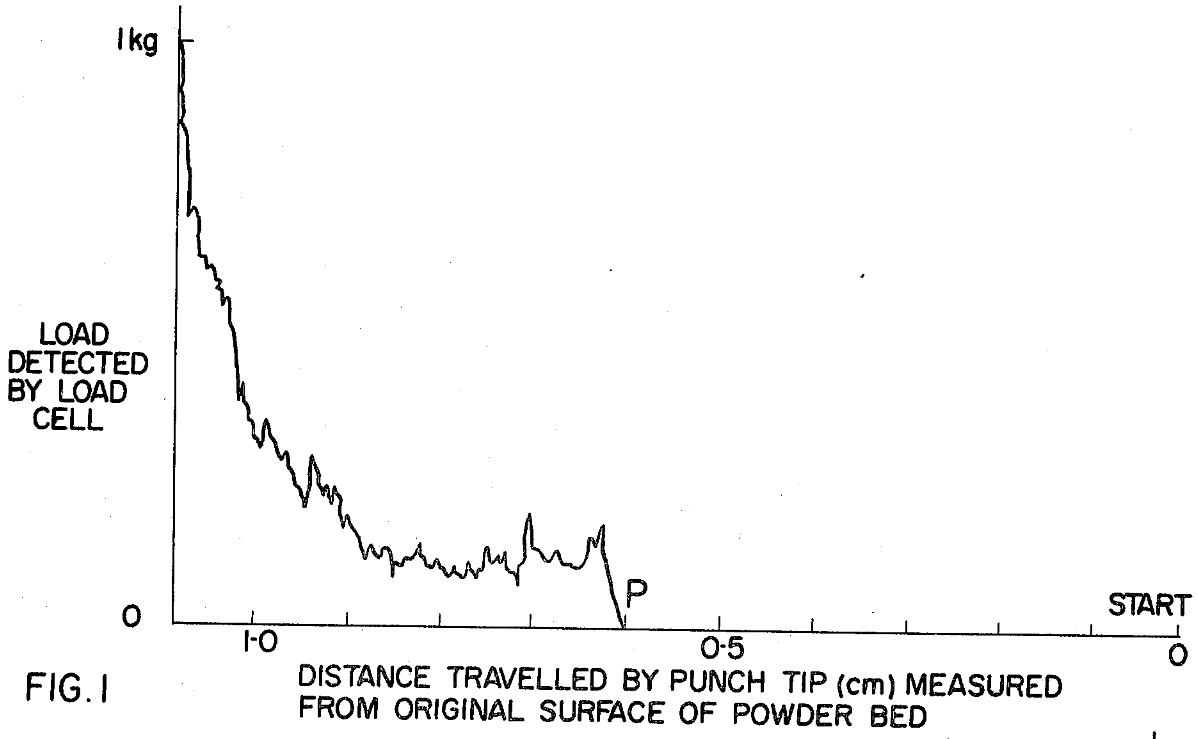
FIG. 1
FIG. 2
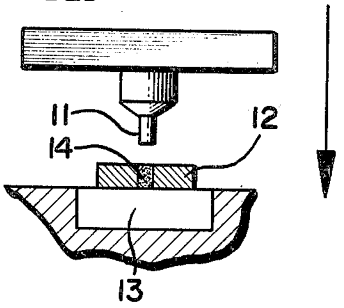
FIG. 3
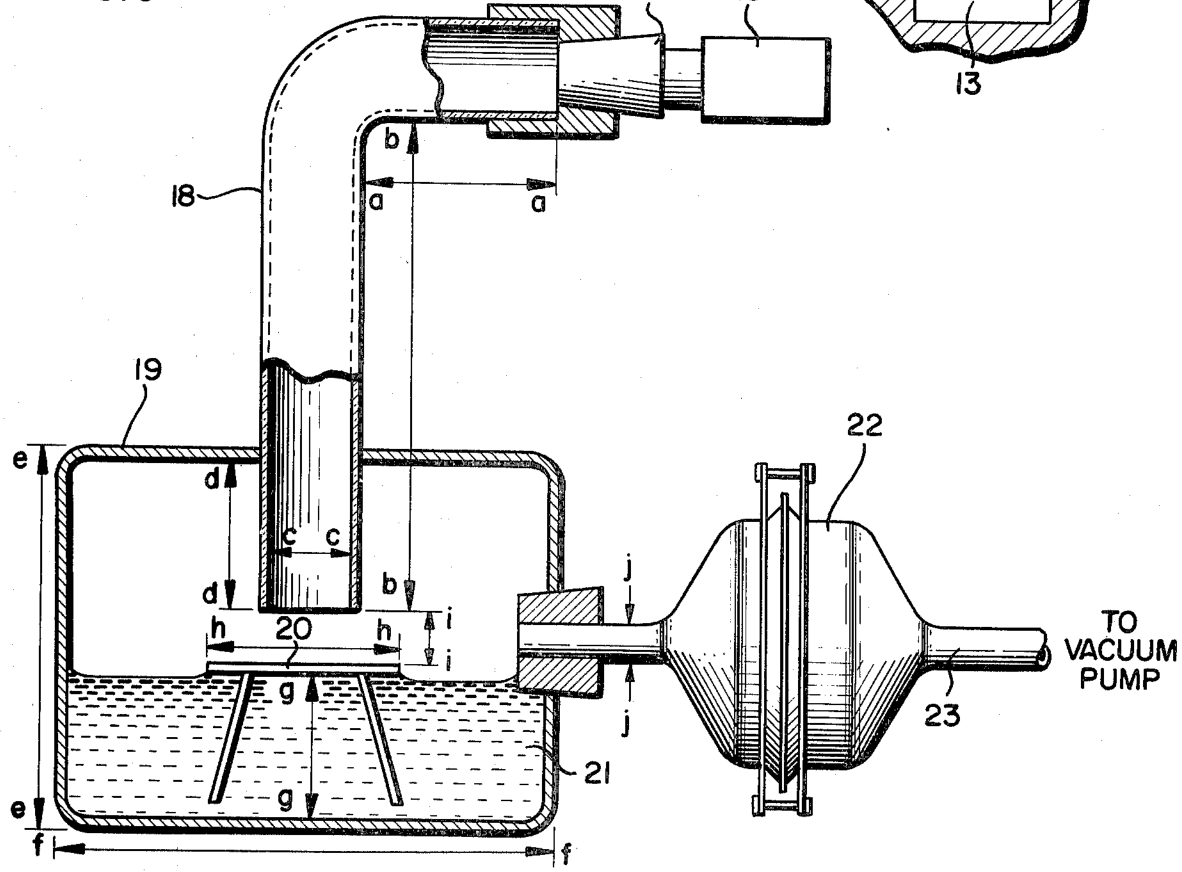

FIG. 4
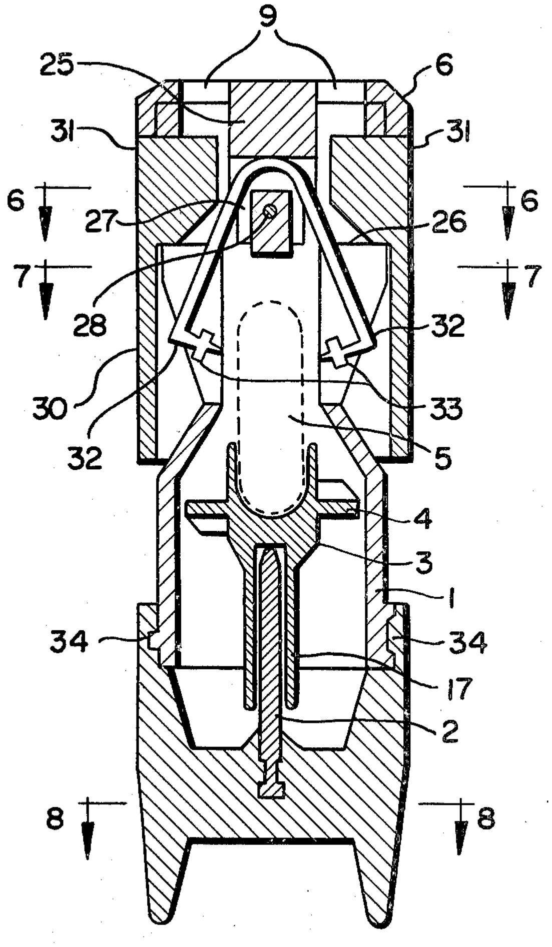
FIG. 5
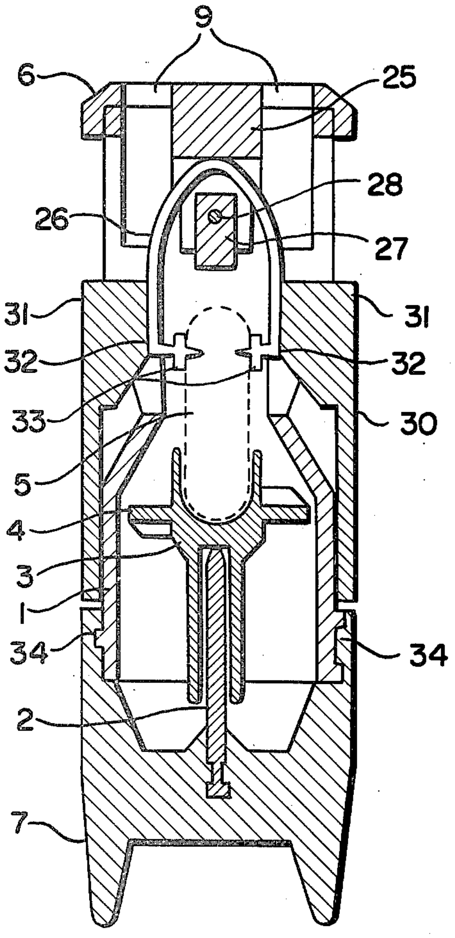
FIG. 6
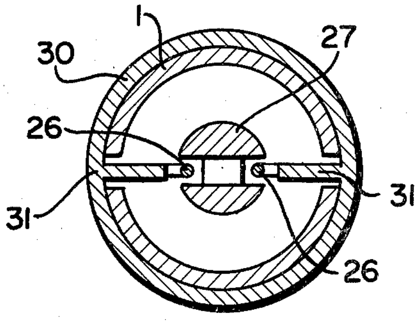
FIG. 7
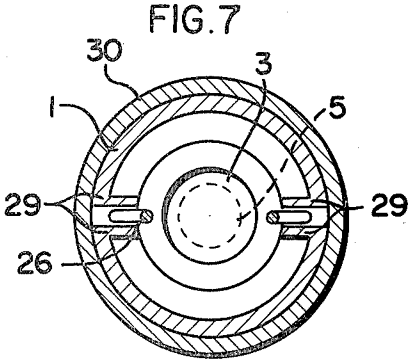
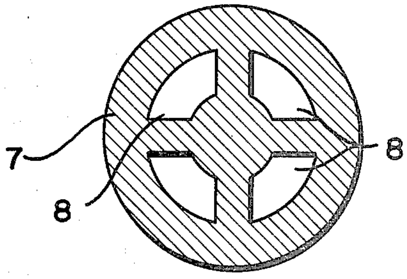
FIG. 8

COMPOSITION FOR TREATING AIRWAY DISEASE

This application is a continuation-in-part of application Ser. No. 599,071, filed July 25, 1975, now abandoned.

The present invention relates to a pharmaceutical composition and its preparation.

In our British Pat. No. 1,182,779 we have described and claimed an insufflator device for use in the administration of powdered medicaments by inhalation comprising a propeller-like device carrying a powder capsule rotatably mounted within a tubular housing by means of a shaft loosely journalled in a tapered bearing tube, the housing having a mouthpiece whereby a user can inhale air through the device. With that device, and other devices, e.g. that described in British Pat. No. 1,331,216, a user inhales air through the device which causes a powder container mounted therein to rotate. Powder within the container is fluidised and dispensed into the air stream which is inhaled by the user. For optimum dispensing it has been found that the powdered medicament particles should be comparatively free-flowing and yet should have an ultimate particle size of less than about ten microns to ensure adequate penetration of the medicament into the lungs of the user. These two requirements are prima facie mutually exclusive, since such fine powders are not sufficiently free-flowing. We have now found that this problem can be mitigated or overcome by forming the powdered medicament into small soft pellets or granules which will fluidise satisfactorily within the container and yet which are of sufficiently low internal coherence to break up into finer particles of medicament of a therapeutically effective size in the turbulent airstream around the outside of the container. The formation of the medicament into soft pellets or granules also aids the filling of the medicament into capsules and can enable diluents such as coarse lactose, which have in the past been incorporated into powder inhalation compositions, to be omitted from the composition.

Accordingly, the present invention provides a medicament in pellet or granule form, wherein the pellet or granule is soft, is from 10 to 1,000, preferably 30 to 500, microns in diameter and comprises an agglomeration of individual medicament particles, at least 90% and preferably at least 95% by weight of which have a diameter of less than 10 microns.

We prefer the pellets or granules to have (i) a 'Total Transmitted Load Reduction' (as hereinafter defined) of greater than 100, preferably greater than 400, more preferably greater than 800 and most preferably greater than 1,000 gms, and/or (ii) a product of 'Total Transmitted Load Reduction' (as hereinafter defined) and 'Response Lag' (as hereinafter defined) of greater than 30, preferably greater than 40, and more preferably between 40 and 1,000 g/cms, and/or (iii) a 'Response Lag' (as hereinafter defined) of at least 0.3, preferably of at least 0.4, and more preferably of between 0.4 and 0.8 cms.

The soft pellet or granule preferably has an internal coherence such that the pellet or granule remains intact when filled into a container, e.g. a capsule, using automatic or semi-automatic filling machines, under conditions of transport and storage, and when fluidised within a container in the device from which it is intended to dispense the pellets or granules and yet may be broken up into particles of a therapeutically effective size outside the container as it discharges from the container.

The medicament in the soft pellets or granules of the invention may be selected from a wide range of powdered medicaments and may be in amorphous or crystalline form and may have been comminuted, e.g. ground, and, if necessary, classified or seived, e.g. on an air jet sieve, to obtain a suitable size or may have been made by direct crystallisation to the desired size. However, it is preferred that the medicament be one which is to be administered by inhalation and which has a substantial number of particles, e.g. greater than 95% by weight, of less than 10 microns, e.g. from 0.01 to 10, and preferably from 1 to 4, microns diameter, before incorporation into the soft pellets of the invention. Desirably the individual medicament particles are self-agglomerative as is usually the case with a hygroscopic material. Examples of suitable medicaments include those suitable for the inhalation (e.g. oral or nasal inhalation) treatment of allergic airway diseases such as pharmaceutically acceptable salts of 1,3-bis(2-carboxychromon-5-yloxy)propan-2-ol, pharmaceutically acceptable salts of 1,3-bis(2-carboxychromon-7-yloxy)-propan-2-ol, sympathomimetic amines (e.g. isoprenaline, ephedrine, or isoetharine and salts thereof), antibiotics (e.g. tetracycline), steroids, enzymes, vitamins and antihistamines. If desired a mixture of medicaments, e.g. a mixture of the disodium salt of 1,3-bis(2-carboxychromon-5-yloxy)propan-2-ol (commonly known as sodium cromoglycate, disodium cromoglycate or cromolyn sodium) and isoprenaline, may be used. The pellets or granules of the invention may also, if desired, be used for administration topically, e.g. to the skin, or oesophagaeally.

The pellets or granules may contain other ingredients, e.g. diluents colouring and flavouring agents. Where the medicament is not self agglomerative, e.g. hygroscopic, it may be desirable to incorporate a small portion of a binder into the soft pellets or granules. Suitable binders include acacia gum, tragacanth gum, celluloses such as salts and ethers of carboxymethylcellulose, dextrans and sugar solutions. Where the medicament is not easily wetted it may be desirable to incorporate a small proportion of a surface active agent into, and/or to use a solvent in the preparation of, the soft pellets or granules. In general we prefer not to use a binder, surface active agent or solvent (other than water) in the soft pellets or granules.

When the medicament is hygroscopic a small proportion of water, which, if necessary, is added to the medicament in the vapour phase for pellets and in the liquid phase for granules is usually sufficient to act as binder. The moisture content of the material may be adjusted according to the physical properties or the particular material, for example, for disodium cromoglycate we prefer the soft pellets or granules to contain less than 15%, and preferably from 8 to 11% by weight of water.

The size of the soft pellets or granules of the invention may be varied within the range given above to suit the devices from which they are to be dispensed. For a given device there is an optimum pellet or granule size for optimum fluidisation of the soft pellets or granules and this may be readily determined by simple tests, e.g. by assessing the fluidisation of extremely strong pellets or granules within the device which it is intended to use. We have also found that optimum dispensing of the soft pellets or granules is related to the size of the hole in the container through which the pellets or granules are to issue. We prefer that the pellets or granules have a size of from one-twentieth to one-fifth of the diameter of the hole, which usually has a diameter of from 500 to 2,000, e.g. about 700 to 1,500 microns.

However, the internal coherence of the soft pellets or granules may affect the desired size of the soft pellets or granules since, as a generality, the larger the pellet or granule the more internally coherent it must be in order to survive the forces experienced during fluidisation and it may be that the optimum pellet or granule size (as determined by criteria other than internal coherence) would require that the pellet or granule be so internally coherent for fluidisation that is not broken up after it leaves the container. The optimum size of the soft pellet or granule may therefore have to be reduced in order that a suitable internal coherence value may be used. However, as a general guide, we have found that satisfactory soft pellets or granules for use in insufflators of the type described in British Pat. No. 1,182,779 (commercially available under the Registered Trade Mark 'Spinhaler') and powered by human inhalation have a mean size in the range of from 50 to 250 microns, preferably a mean size in the range 120 to 160 microns and most preferably a mean size of about 140 microns.

As indicated above, the necessary internal coherence to be possessed by the soft pellet or granule is a function of the conditions to be experienced both inside the container during fluidisation and outside the container for achieving the break-up of the soft pellets or granules. Large soft pellets or granules must be of comparatively high internal coherence to withstand the forces generated during fluidisation in the container and yet must not be so strong that they do not break-up outside the container to form finer particles of a therapeutically effective size, which is preferably less than about 10 microns, e.g. from about 0.01 to 10, and preferably from 1 to 4, microns in diameter, for medicaments which are to penetrate deep into the lungs of a subject. The internal coherence of the soft pellet or granule may therefore be varied over quite a wide range depending upon the energy available for breaking-up the soft pellet or granule, and its size. The minimum internal coherence which may be possessed by the soft pellets or granules will depend on their size and density, and on the forces to which the soft pellets or granules are subject during fluidisation within the container. The internal coherence for a given case may be determined by simple test and modified as appropriate.

The soft pellets or granules should be sufficiently coherent to be filled into containers, transported and stored, since appreciable break-up of the soft pellets or granules should not occur under these conditions.

From the above, it will be appreciated that soft pellets or granules having satisfactory properties may be obtained from a number of permutations of the size and coherence. By way of an example, we have found that for soft pellets or granules which are to be dispensed from a gelatine capsule 6.4 mm in diameter and having two holes 0.8 mm in diameter in a shoulder thereof mounted in a device (commercially available under the Registered Trade Mark 'Spinhaler') according to British Pat. No. 1,182,779 having a drawn wire shaft 2.03 mm diameter journalled in a hard nylon bearing tube 13 mm long and having an internal diameter of 2.08 mm at its inner end (i.e. that end housing the free end of the shaft) and of 2.44 mm at its other end, and wherein the capsule is rotated about its axis at a speed of about 1,800 rpm by an air stream having a flow rate of 60 liters per minute it is desirable that the pellets have a mean size of about 140 microns. It is especially preferred that the pellets or granules are made from disodium cromoglycate.

The soft pellets or granules are preferably such that when put up in gelatine capsules 6.4 mm in diameter each containing 20 mg of the medicament as soft pellets or granules they meet the criteria set out in the tests (a) and (b) below:

(a) Dispersion test

The filled capsules are mounted in the capsule holder of the powder insufflator (having the specific dimensions set out immediately above) of British Pat. No. 1,182,779 and pierced to produce two holes of 0.8 mm diameter in a shoulder of the capsule.

It should be understood that, unless otherwise qualified, the term "powder insufflator" when used herein and in the appended claims refers to the device shown in said British patent and having said specific dimensions.

The powder insufflator is illustrated in FIGS. 4, 5, 6, 7 and 8.

FIGS. 4 and 5 are longitudinal sections through the insufflator in the non-piercing and the piercing positions respectively;

FIG. 6 is a cross-sectional view at line A—A in FIG. 4;

FIG. 7 is a cross-sectional view at line B—B in FIG. 4; and

FIG. 8 is a cross-sectional view at line C—C in FIG. 4.

In FIGS. 4, 5, 6, 7 and 8 the device comprises a hollow body member 1 of generally circular cross-section provided at one end with an end piece 6 which is perforated by air passages 9, and at the other end with a mouthpiece 7 provided with air passages 8. End piece 6 is firmly attached to body member 1, for example it may be glued thereto, and mouthpiece 7 is removably attached to body member 1 by means of co-operating screw threads 34 in body member 1 and mouthpiece 7.

End piece 6 has a central projection 25 in a slot in which is mounted resilient piercing member 26. Piercing member 26 is retained in the slot in projection 25 by means of retaining block 27 which is, in turn, held in position in the slot by means of pin 28. The arms of resilient piercing member 26 are located in slots in the walls of body member 1 and in guideways formed by guide members 29 extending inwardly from 75 the inner surface of body member 1.

Mounted in mouthpiece 7 and extending into body member 1 is shaft 2 on which is mounted, by means of bearing tube 17, propeller-like member 3 having blades 4 and a cup-like depression for receiving gelatine capsule 5.

Slidably mounted on body member 1 is tubular member 30 having cam-like projections 31 extending inwardly through the slots in body member 1. When member 30 is slid from the position shown in FIG. 4 to that shown in FIG. 5 cam-like projections 31 engage with the arms of resilient piercing member 26 to force them inwards and thus to force piercing projections 32 into contact with the surface of capsule 5 and finally to pierce capsule 5 as shown in FIG. 5, the depth of piercing being limited by stops 33. When the member 30 is slid back from the position shown in FIG. 5 to that shown in FIG. 4 the resilience of member 26 causes the arms to spring apart and to resume the position shown in FIG. 4.

In operation, the device is first loaded with capsule 5 by unscrewing mouthpiece 7 from body member 1 and placing capsule 5 in the cup-like depression in propeller-like device 3. Mouthpiece 7 is then screwed back into body member 1 and the device is ready for use.

In use, the capsule 5 is pierced by sliding member 30 from the position shown in FIG. 4 to that shown in FIG. 5 and then back to the position shown in FIG. 4.

The dispersion of the medicament-in the cloud delivered by the insufflator is determined using a modified version of the multistage liquid impinger described in British Pat. No. 1,081,881. The modified impinger is illustrated in FIG. 3 which represents a cross-section through the impinger.

In FIG. 3 the powder insufflator 15 is situated in the rubber sleeve 16, and is thereby connected to the bent glass tube 18. The lower end of the glass tube 18 is inserted into a container 19 which is partially filled with distilled water 21 and has a porous impingement disc 20. Connected to one side of container 19 is a filter unit 22 which in turn is connected to a vacuum pump via tube 23. The dimensions of the device are given below:

| | |
|---|---|
| a—a | 35 mm |
| b—b | 150 mm |
| c—c | 19 mm |
| d—d | 30 mm |
| e—e | 55 mm |
| f—f | 100 mm |
| g—g | 4 mm |
| h—h | 38 mm |
| i—i | 6 mm |
| j—j | 10 mm |

The insufflator is inserted into the upper, horizontal end of the glass tube and air drawn through at 60 liters per minute for 30 seconds. At least five capsules are treated in this manner and the results are averaged. The weight of the medicament collected on the filter, and that in the remainder of the apparatus and in the insufflator is determined spectrophotometrically after solution in an appropriate volume of distilled water (or by any other appropriate method).

The soft pellets or granules disperse satisfactorily if an average total for each capsule of at least 8%, preferably at least 10% and most preferably at least 14% by weight of the medicament are found on the filter of the liquid impinger. Medicament found on the filter represents particles having a size of less than 8.5 microns.

(b) Emptying test

The filled capsules are mounted in the capsule holder of the powder insufflator (having the specific dimensions set out-above and as illustrated in the attached FIGS. 4, 5, 6, 7 and 8) of British Pat. No. 1,182,779 and pierced to produce two holes of 0.8 mm diameter in a shoulder of the capsule. The insufflator is placed in a device adapted to suck air through it for 2.5 seconds, the air flow rate at no time exceeding 60 liters per minute, and being held at 60 liters per minute for at least 2 seconds. The capsule mounted in the insufflator is subjected to 4 sucks as described and the weight of the material remaining in the capsule is determined. The above procedure is repeated 20 times and the average of the results determined.

The soft pellets or granules empty satisfactorily if an average of at least 50%, preferably at least 75% and most preferably at least 90% by weight of the material has emptied from each capsule.

The following tests are also of significance in defining the pellets or granules of the invention:

(c) Response lag

The response lag may be measured by means of a device (available from Instron Limited, Coronation Road, High Wycombe, Buckinghamshire, England as Model TM-SM) for the measurement of the stress/-strain properties of materials. This device is illustrated in FIG. 2 and comprises a punch 11 capable of fitting tightly into a die 12 of 4 mms diameter and of 1.55 cms length. The die is open at the top end, save when the punch is inserted in that end, and is closed at the bottom end by the surface of a load cell 13 connected to a recorder adapted to record loads of from 1 to 1000 g. In operation the material to be tested 14 is filled carefully into the die in such a way as to avoid bridging, and the surface made level with the top of the die. The punch is moved at a constant speed into the die from the top end and the load transmitted to the load cell is recorded graphically. The response lag is defined as the distance in cms that the punch tip travels below the top of the die before a response of 1 g is registered by the load cell.

(d) Total Transmitted Load Reduction

It has also been found that with medicaments according to the invention which disperse satisfactorily the applied load transmitted to the load cell in the device described in (c) above does not increase steadily (see for example FIG. 1). The back track of the curve, or the 'easing' of the load in grams, may be termed the 'Total Transmitted Load Reduction' of the material under test. Thus 'Total Transmitted Load Reduction' may be defined as the sum of the reductions in the transmitted load detected by the load cell while the load recorded as acting on the cell progresses from 0 to 1,000 gms.

(e) Strength test

A measure of the strength of the soft pellets of the invention may be achieved by means of the device described in paragraph (c) above. It has been found that with soft pellets or granules according to the invention a measurement of 10 g on the pressure sensitive plate occurs when the volume of the soft pellets or granules has been reduced by about 25 to 35%, preferably about 30%, of the original volume of the soft pellets or granules and that a measurement of 1 kg on the pressure sensitive plate occurs when the volume of the soft pellets or granules has been reduced by about 50 to 70%, preferably about 60%, of the original volume of the soft pellets or granules.

It has been found that the most useful parameter in the definition of the pellets or granules according to the invention is the product of the 'Total Transmitted Load Reduction' and the 'Response Lag'.

The pellets and granules according to the invention have a lower loose bulk density than granules or pellets made by conventional techniques. Thus soft pellets and granules of disodium cromoglycate have a loose bulk density of less than 0.3 g per cc, preferably from 0.2 to 0.3 g per cc, and most preferably from 0.22 to 0.28 g per cc.

From another aspect the invention also provides a capsule, cartridge or like container containing soft pellets or granules of the invention, optionally in association with other pellets, granules or particles. We prefer the container to be loosely filled to less than about 80% by volume, preferably less than about 50% by volume, with the soft pellets or granules of the invention. The soft pellets or granules should of course not be compacted into the container. We prefer the container, e.g capsule, to contain from 10 to 100 mg of the soft pellets or granules. The container may conveniently be pierced (and overcapped, e.g with a plastic overcap) during its manufacture and then used, after removal of the overcap, in an inhalation device which has no piercing mechanism.

Where it is desired to use the pellets or granules of the invention in association with other ingredients such as colourants, sweeteners or carriers such as lactose, these other ingredients may be applied, to or admixed with the pellets or granules using conventional techniques. We prefer the soft pellets or granules of the invention to contain medicament and water only and not to be mixed with any other ingredients.

The soft pellets or granules of the invention may be made by a number of methods.

Thus according to the invention there is provided a method for the manufacture of soft pellets or granules according to the invention, which comprises subjecting particles of medicament (optionally in admixture with any other ingredient it is desired to incorporate into the pellets) which either are intrinsically, or have been rendered, self-agglomerative to a controlled agglomeration. This controlled agglomeration may be carried out by, (a) extruding the particles of medicament through an aperture,
(b) controlled agglomeration in a fluidised bed, or
(c) spray drying a solution or slurry of the medicament.

In method (a) which is the preferred method, finely divided medicament, e.g having a means particle size in the range 0.01 to 10 microns may, if necessary, be subjected to an initial treatment to cause the powder particles to be self-agglomerative. Thus where the medicament is of a hygroscopic nature, the treatment may be carried out by exposing the powder particles to water.

When soft pellets are required the powder particles may be subjected to a humid atmosphere, for examaple at a temperature of from about 15° to 50° C. Whilst the amount of water required to achieve adequate self-agglomerative properties may vary from medicament to medicament, it will not usually be necessary to increase the water content of the powder beyond about 15% by weight, e.g to from 5 to 10% when soft pellets are required. Where the medicament is non-hygroscopic, the necessary self-agglomerative properties may be imparted by the addition of a pharmaceutically acceptable binder, e.g one selected from those mentioned earlier, or by treating the powder with a liquid (under carefully controlled conditions), which may be evaporated to produce bridges of a solid residue binding the powder particles, or which causes adequate interparticle contact. It will be appreciated that the nature of the binder may affect the coherence of the resultant pellet or granule formed from treated medicament. A binder solution may, if desired, be used with a hygroscopic medicament in order to improve the internal coherence of the resultant pellet or granule. After the particles have been rendered self-agglomerative, they are passed (optionally after being rolled in for example a drum or pan for a controlled time) through an aperture of approximately the size of the desired pellets, e.g. they are forced through the apertures of a vibrating sieve which is of similar mesh aperture to the desired final pellet or granule size. The product of this passage through an aperture are shaped pre-pellets of the medicament.

When soft granules are required the powder particles may be mixed with an excess of a suitable solvent, e.g. liquid water, and the moistened material passed through an aperture, e.g. a sieve such as a vibrating sieve, of approximately equal to or larger than the mesh size required in the final granules and then drying the resulting sieved material to the desired final solvent, e.g. water, content. The material may then be dry granulated to give the required product.

When it is desired to incorporate another ingredient, e.g. a binder, into the soft granules the other ingredient may conveniently either be mixed with the medicament before it is moistened or may be incorporated in the solvent used to moisten the medicament.

The amount of water, or other solvent, used in the granulation cam, under certain circumstances, be critical. Thus we have found that with di-sodium cromoglycate (DSCG) use of greater than about 25% by weight of water (measured on dry DSCG) causes the granules to be too strong and not to have satisfactory dispersion properties. We therefore prefer to use from about 12 to 25%, and preferably from 17 to 23% by weight of water in the granulation of di-sodium cromoglycate.

The drying is preferably effected in a preheated forced convection hot air oven. The temperature of drying is desirably from 60 to 100° C, and more especially from 80 to 90° C.

The soft granules may also be made by controlled agglomeration of the medicament in a fluidised bed or by spray drying a solution or slurry of the medicament.

In process (b) the fine particles of medicament to be formed into pellets or granules may be suspended, together with any other ingredients it is desired to incorporate in the pellets or granules, in a gas stream in a fluidised bed apparatus. When a hygroscopic material is to be formed into pellets or granules the water content of the solid material may be adjusted by variation of the humidity of the gas stream passing through the fluidised bed or by spraying water into the bed. The medicament may be treated in the fluidised bed for a time and under conditions sufficient to produce pre-pellets or granules of the desired internal coherence and size.

In process (c) a solution or more preferably a slurry, of the medicament may be spray-dried to produce a soft granule. We prefer to use a slurry of discrete medicament particles of the desired fine particle size, the slurry also containing any other ingredients it is desired to incorporate in the granules. The liquid in the slurry is preferably a non-solvent or a poor solvent for the medicament so that no, or not many, medicament bridges are formed between the medicament particles during the spray drying. When a controlled amount of water is desired in the product a correspondingly greater amount of water may be included in the liquid in the slurry.

The extent of compaction of the treated powder during the controlled agglomeration will vary according to the method and powder used in the agglomeration. However, as a guide, we have found that suitable pre-pellets may be formed by process (a) from a powder of disodium cromoglycate containing from about 8 to 10% by weight of water, by forcing the powder through a sieve having apertures of about 150 micron size.

The pre-pellets produced by any of the above processes may, if desired or necessary be subjected to tumbling and agitation using conventional methods until the desired size, shape and coherence of the pellets are achieved. We prefer a proportion, e.g a majority, of the soft pellets, and especially soft pellets of disodium cromoglycate, to be approximately spherical. Conveniently the tumbling and agitation are carried out in a pan or drum type of pelletising machine. The treatment of the pre-pellets in such a machine is carried out until the majority of pellets in the charge have a size within the desired range. The size of the pre-pellets used and the conditions used in their agitation and tumbling may be varied in known manner to achieve the desired final size of soft pellet. The time for which the pellets are tumbled is, in certain circumstances, of importance to the production of viable soft pellets. The effect of the tumbling and agitation of the pellets is in general to strengthen them and increase their size slightly and to make them more nearly spherical in shape.

As indicated above the final product which issues from the agitation or tumbling step will have a range of sizes about the desired mean size. The product may be classified, e.g sieved, to remove over and under sized material. The over and under sized materially may be broken down into very fine particles and recycled to the agglomeration stage if desired.

The final soft pellets or granules may be put up in any suitable form of container such as a capsule or cartridge. Where it is desired to use the pellets or granules of the invention in association with other ingredients such as colourants, sweeteners or carriers such as lactose, these other ingredients may be applied to or admixed with the pellets or granules using conventional techniques. We prefer the soft pellets or granules of the invention to contain medicament and water only. The soft pellets or granules may also be used in admixture with up to 75% by weight of free particles of medicament having a diameter of from 0.01 to 10 microns.

According to our invention we also provide a method of application of a medicament, e.g disodium cromoglycate, to a patient by way of inhalation, the medicament being dispersed into an air stream, characterised in that a pierced container containing soft pellets or granules according to the invention is rotated and vibrated in an air stream which is inhaled by the patient. The rotation and vibration may conveniently be produced by any one of a number of devices, e.g the device of British Pat. Nos. 1,122,284 and 1,182,779. Disodium cromoglycate is known to be of use in the treatment of asthma and rhinitis.

In this specification the term 'pellet' is used to denote an agglomerate which is held together by interparticulate (e.g Van der Waal's) forces and is typically made by a process involving water vapour. Pellets are in general spherical in shape. The term 'granule' is used to denote an agglomerate which is held together by interparticle bridges. In the case of a soft granule these bridges are brittle. Granules can be of almost any shape. Granules are typically made by overwetting the medicament with solvent, e.g water, and then removing some of the solvent.

Medicament in soft pellet form represents a preferred embodiment of the invention.

The invention will now be illustrated by the following Examples in which all parts and percentages are by weight unless otherwise stated.

EXAMPLE 1

The moisture content of micronised disodium cromoglycate having at least 98% thereof of particle size less than 10 microns and having a mass median diameter of from 1 to 3 microns was adjusted from an initial value of from 4 to 6% by weight to a value of about 9.5% by weight by exposure of the powder on a tray in an atmosphere of relative humidity 33% at 18° to 24° C.

After the desired moisture content had been achieved, the treated powder was (after an optional initial rolling in a drum pelletiser) tipped onto a 150 micron aperture stainless steel sieve screen mounted in a Russel vibratory sifter operating at a frequency of 1,000 cycles per second. The powder on the screen was forced through the sieve apertures using a stainless steel spatula pushed across the surface of the screen. The material issuing from the sifter as particles with a mean particle diameter of about 150 microns was fed directly to a drum pelletiser adapted to rotate about a horizontal axis. The drum of the pelletiser was approximately 0.3 m in internal diameter and 0.37 m long with one end closed and the other end provided with frusto conical shoulder leading to a 0.18 m orifice through which material could be charged to or removed from the drum. The interior of the drum was highly polished. Two kilograms of the material from the sifter were loaded into the drum which was then rotated at a peripheral speed of 0.38 m per second ±0.025 m per second for 15 minutes. At the end of this time the soft pellets had a mean particle diameter of 135 microns and not more than 10% by weight was retained on a 350 micron aperture sieve and not less than 90% by weight was retained on a 63 micron aperture sieve. The moisture content of the final soft pellets was in the range 8.5 to 10.5% by weight.

It will be appreciated that those steps of the process carried out after adjustment of the moisture content of the initial powder should be carried out under conditions of controlled humidity so as not to alter the water content of the powder appreciably. The water used in the process should be sterile and the air used in the process should be Class 100 air.

The soft pellets produced by the above procedure are approximately spherical, and have an open and loose structure and a fluffy surface when viewed under a microscope.

Up to 90 mg, e.g 40 to 60 mg, of the above soft pellets were placed in a gelatine capsule having two holes 0.8 mm in diameter pierced in the shoulder thereof which was mounted in a device as described in British Pat. No. 1,187,779 having the detailed construction and dimensions referred to above. When air at a flow rate of 60 liters per minute was passed through this device, it was found that the charge in the capsule was consistently completely dispensed into the airstream and broken up to provide a cloud of very fine particles suitable for inhalation.

By way of contrast, when the initial micronised powder from which the pellets had been prepared was tested under identical conditions, comparatively little of the powder was dispensed and the amount dispensed varied inconsistently from test to test.

Similar results were obtained when isoprenaline sulphate and tetracycline were subjected to the procedure of the Example to obtain soft pellets.

EXAMPLE 2

Using the device illustrated in FIG. 2 and, pellets of di-sodium cromoglycate according to Example 1 a Response lag of greater than 0.4 cms, a Total Transmitted Load Reduction of greater than 900 gms and a dispersion of greater than 10% were obtained.

EXAMPLE 3

1,000 g of micronised disodium cromoglycate of determined water content was placed in the bowl of a planetary mixer. The calculated amount of water to bring the moisture content of the disodium cromoglycate to within the desired range was then added gradually, the sides of the mixer bowl being scraped regularly to ensure even moisture distribution. The damp disodium cromoglycate was then passed through a vibrating sieve having a mesh size of 1,000 microns. The product was then dried in a preheated forced convection hot air oven at 85° C. for 2 hours until the moisture content of the granules was in the range 5 to 8% by weight. The granules were then sieved through a 250 micron screen. The resulting granules were found to flow well and could be filled easily into gelatin capsules.

EXAMPLE 4

Using the device illustrated in FIG. 2, granules of disodium cromoglycate produced according to Example 3, and the Dispersion Test as previously described, dispersions of greater than 10% were obtained for granules made using from 10 to 25% by weight water at the granulation stage. These granules had response lags of greater than 0.3 cms and a Total Transmitted Load Reduction of greater than 100 gms.

EXAMPLE 5

The moisture content of micronised 1,3-bis(2-carboxychromon-7-yloxy)propan-2-ol di-sodium salt having at least 98% thereof of particle size less than 10 microns and having a mass median diameter of from 1 to 3 microns was adjusted from an initial value of less than 5% by weight to a value of about 6.5% by weight by exposure of the powder on a tray in an atmosphere of relative humidity 44% at 18° to 24° C.

After the desired moisture content had been achieved, the treated powder was tipped onto a 100 mesh stainless steel sieve screen mounted in a Russel vibratory sifter operating at a frequency of 1,000 cycles per second. The powder on the screen was forced through the sieve apertures using a stainless steel spatula pushed across the surface of the screen. The material issuing from the sifter as particles with a mean particle diameter of about 150 microns was fed directly to a drum pelletiser adapted to rotate about an horizontal axis. The drum of the pelletiser was approximately 12 inches in internal diameter and 16 inches long with one end closed and the other end provided with frusto conical shoulder leading to a 7 inch orifice through which material could be charged to or removed from the drum. The interior of the drum was highly polished. Two kilograms of the material from the sifter were loaded into the drum which was then rotated at a peripheral speed of 75 feet per minute ±5 feet per minute for 15 minutes. At the end of this time the pellets had a mean particle diameter of 135 microns and not more than 2% by weight was retained on a 60 BSS sieve and not less than 90% by weight was retained on a 240 BSS mesh sieve. The moisture content of the final pellet was in the range 5.5 to 7.5% by weight.

Those steps of the process carried out after adjustment of the moisture content of the initial powder were carried out under conditions of controlled humidity so as not to alter the water content of the powder appreciably.

The above pellets were placed in a gelatine capsule having two holes 0.6 mm in diameter pierced in the shoulder thereof which was mounted in a device as described in British Pat. No. 1,187,779 having the construction and dimensions referred to above. When air at a flow rate of 50 liters per minute was passed through this device, it was found that the charge in the capsule was consistently completely dispensed into the airstream and broken up to provide a cloud of very fine particles suitable for inhalation.

By way of contrast, when the initial micronised powder from which the pellets had been prepared was tested under identical conditions, comparatively little of the powder was dispensed from the capsule and the amount dispensed varied inconsistently from test to test.

I claim:

1. A pharmaceutical composition adapted to be fluidized into a gas stream for inhalation treatment of airway disease, said composition being in the form of soft pellets or granules having a diameter of about 30 to 500 microns, said pellets or granules comprising a therapeutically effective proportion of a solid medicament useful for treating said disease, each of said pellets or granules being an agglomeration of individual particles of said medicament, at least 90% of said particles having a diameter less than 10 microns.

2. A composition according to claim 1, wherein the pellets or granules have a 'Total Transmitted Load Reduction' of greater than 100 g.

3. A composition according to claim 1, wherein the pellets or granules have a product of 'Total Transmitted Load Reduction' and 'Response Lag' of greater than 30 g/cms.

4. A composition according to claim 1, wherein the pellets or granules have a 'Response Lag' of at least 0.3 cms.

5. A composition according to claim 3, wherein the product of 'Total Transmitted Load Reduction' and 'Response Lag' is greater than 40 g/cms.

6. A composition according to claim 5, wherein the product of 'Total Transmitted Load Reduction' and 'Response Lag' is between 40 and 1,000 g/cms.

7. A composition according to claim 1, comprising a plurality of soft pellets or granules of mean size of from 120 to 160 microns.

8. A composition according to claim 1, comprising an inhalation medicament for treatment of asthma or rhinitis.

9. A composition according to claim 8, wherein the inhalation medicament comprises cromolyn sodium.

10. A composition according to claim 1 comprising less than 15% by weight of water.

11. A composition according to claim 1, wherein the soft pellet is spherical.

12. A capsule containing a composition according to claim 1, the capsule containing from 10 to 100 mg of the composition in soft pellet or granule form and being loosely filled to less than 80% by volume with the composition in soft pellet or granule form.

13. A medicament in pellet or granule form adapted to be fluidized into a gas stream for inhalation treatment of airway disease characterised in that the pellet or granule is soft, is from 30 to 500 microns in diameter and comprises an agglomeration of individual medicament particles at least 90% of which have a diameter of less than 10 microns, wherein an average of at least 75% by weight of the medicament empties from 20 capsules each containing 20 mg of medicament mounted in a powder insufflator through which air is drawn 4 times, each time for 2.5 seconds at a rate at no time exceeding 60 liters per minute and being held at 60 liters per minute for at least 2 seconds.

14. A medicament adapted to be fluidized into a gas stream for inhalation treatment of airway disease in pellet or granule form characterised in that the pellet or granule is soft, is from 30 to 500 microns in diameter and comprises an agglomeration of individual medicament particles at least 90% of which have a diameter of less than 10 microns, wherein when at least 5 capsules each containing 20 mg of medicament mounted in a powder insufflator through which air is drawn at a rate of 60 liters per minute for 30 seconds disperse on average at least 8% by weight medicament particles having a particle size of less than 8.5 microns, and an average of at least 75% by weight of the medicament empties from 20 capsules each containing 20 mg of medicament mounted in said insufflator through which air is drawn 4 times, each time for 2.5 seconds at a rate at no time exceeding 60 liters per minute and being held at 60 liters per minute for at least 2 seconds.

15. A composition in pellet or granule form adapted to be fluidized into a gas stream for inhalation treatment of airway disease characterised in that the pellet or granule is soft, is from 30 to 500 microns in diameter and comprises an agglomeration of individual medicament particles at least 90% of which have a diameter of less than 10 microns, wherein when the pellets are loosely filled into a die of 4 mm diameter and 1.55 cm length closed at the bottom and by a pressure sensitive plate and a punch is moved at constant speed into the die from the top end a measurement of about 10 g on the pressure sensitive plate occurs when the volume of the pellets or granules has been reduced by 25 to 35% and wherein a measurement of about 1 kg on the pressure sensitive plate occurs when the volume of the pellets or granules has been reduced by 50 to 70%.

16. An inhalation medicament in pellet or granule form for oral or nasal inhalation characterised in that the pellet or granule is soft, is from 30 to 500 microns in diameter and comprises an agglomeration of individual medicament particles at least 90% of which have a diameter of less than 10 microns, said pellet or granule being essentially free of excipients.

* * * * *